(12) United States Patent
Perovitch et al.

(10) Patent No.: US 8,846,083 B2
(45) Date of Patent: Sep. 30, 2014

(54) METHOD FOR THE DIFFUSION OF MOLECULES WHICH ARE INSOLUBLE IN AN AQUEOUS MEDIUM AND COMPOSITION USING SAID METHOD

(76) Inventors: Philippe Perovitch, Lege Cap Ferret (FR); Marc Maury, Saint Medard en Jalles (FR)

(*) Notice: Subject to any disclaimer, the term of this patent is extended or adjusted under 35 U.S.C. 154(b) by 2067 days.

(21) Appl. No.: 10/588,005

(22) PCT Filed: Feb. 1, 2005

(86) PCT No.: PCT/FR2005/050062
§ 371 (c)(1),
(2), (4) Date: Aug. 1, 2006

(87) PCT Pub. No.: WO2005/074885
PCT Pub. Date: Aug. 18, 2005

(65) Prior Publication Data
US 2007/0110801 A1    May 17, 2007

(30) Foreign Application Priority Data
Feb. 3, 2004 (FR) .................................... 04 50194

(51) Int. Cl.
*A61K 9/20* (2006.01)
*A61K 31/19* (2006.01)
*A61K 31/205* (2006.01)
*A61K 9/00* (2006.01)
*A61K 31/00* (2006.01)
*A61K 31/192* (2006.01)

(52) U.S. Cl.
CPC .............. *A61K 31/00* (2013.01); *A61K 31/205* (2013.01); *A61K 9/0056* (2013.01); *A61K 9/006* (2013.01); *A61K 31/192* (2013.01)
USPC ............................ 424/464; 514/569; 514/570

(58) Field of Classification Search
CPC ... A61K 31/00; A61K 31/192; A61K 31/205; A61K 9/0056; A61K 9/006; A61K 9/2054; A61K 31/19
USPC .................................. 424/464; 514/569, 570
See application file for complete search history.

(56) References Cited

U.S. PATENT DOCUMENTS

| | | | |
|---|---|---|---|
| 5,206,029 A | 4/1993 | Brune et al. | |
| 6,056,944 A * | 5/2000 | Finidori | 424/49 |

FOREIGN PATENT DOCUMENTS

| | | | |
|---|---|---|---|
| CA | 2243522 A1 | 7/1997 | |
| EP | 0 137 668 | 4/1985 | |
| EP | 0 159 604 | 10/1985 | |
| EP | 0 523 847 | 1/1993 | |
| EP | 0 935 961 | 8/1999 | |
| GB | 1 103 686 | 2/1968 | |
| WO | WO 92/00725 | 1/1992 | |
| WO | WO 95/07103 * | 3/1995 | A61K 45/06 |
| WO | WO 95/08988 | 4/1995 | |
| WO | WO 95/15137 | 6/1995 | |
| WO | WO 97/04808 | 2/1997 | |
| WO | WO 97/20572 | 6/1997 | |
| WO | WO 97/26866 | 7/1997 | |
| WO | 9852540 A1 | 11/1998 | |
| WO | WO 98/52539 | 11/1998 | |
| WO | WO 02/067916 | 9/2002 | |
| WO | WO 02/083119 | 10/2002 | |
| WO | WO 03/043600 | 5/2003 | |

OTHER PUBLICATIONS

Tsunematsu et al., "Synthesis and the Stereoselective Enzymatic Hydrolysis of Flurbiprofen-Basic Amino Acid Ethyl Esters", Journal of Drug Targeting, 1995, vol. 2, pp. 517-525.

* cited by examiner

*Primary Examiner* — Aradhana Sasan
(74) *Attorney, Agent, or Firm* — Young & Thompson

(57) ABSTRACT

A process for local permucosal diffusion of amino acid salts of low dosage lipophlic non-steroidal anti-inflammatory or anti-mycotic molecules for an aqueous medicine for the treatment of bucco-pharyngeal ailments is disclosed. Compositions and tablets implementing this diffusion process are also disclosed.

13 Claims, No Drawings

METHOD FOR THE DIFFUSION OF MOLECULES WHICH ARE INSOLUBLE IN AN AQUEOUS MEDIUM AND COMPOSITION USING SAID METHOD

This invention relates to a process for diffusion through the mucous membranes of the mouth and the throat of insoluble molecules in an aqueous medium but a process that also allows the passage of certain active ingredients in the vascular system via the sublingual permucosal pathway. The invention also covers a composition that implements this process in particular for the treatment of buccopharyngeal ailments.

By way of example, the inflammatory and painful ailments of the buccopharyngeal cavity are detrimental to patients, and it is necessary to note that the pharmacopeia is poor for providing effective rapid relief that is of sufficient duration and that limits the secondary effects.

These buccopharyngeal ailments are of various origins and develop in the front portion, on the mucous membranes of the floor and walls of the mouth or on the back portion, on the pharyngeal mucous membrane.

The buccopharyngeal cavity being a constant and preferred path of access for all the germs and irritants brought in via the respiratory and alimentary tracts, this mucous membrane zone is also a preferred development site of bacterial populations, of more or less pathogenic viruses that warrant a treatment of the inflammations that they produce.

These inflammations can be more or less significant and can cause invalidity ranging from the simple feeling of localized unease to the presence of macroscopically visible lesions of the type of those generated by aphtoses.

Such inflammations are often lacking in important clinical signs such as fever or ganglial formations.

Current treatments provide the use of anti-inflammatory and/or analgesic products with local administration: sprays, lozenges that dissolve in the mouth, and mouthwashes.

As for available medications, they have become extremely limited since the disappearance of many products by way of medication, i.e., compositions that have received marketing licenses.

Thus, the products that comprise combinations of enzymes, lysozyme, papain, contact anesthetics or local antibiotics have lost their AMM or will lose it.

Actually, such products as the anesthesias, by masking the pain rather than treating the ailment, conceal the reality of the inflammation.

One solution consists in resorting to powerful anti-inflammatory agents that make it possible to reduce the pain while also treating the associated inflammations.

Such active ingredients are administered via the digestive tract with all of the associated drawbacks.

The active ingredient is therefore to be metabolized by the organism inducing a generalized distribution of the molecule throughout the organs and tissues.

This broad diffusion is wasteful for the most part since to treat the 2% representing the buccopharyngeal cavity, 100% of the organism is treated.

Actually, it seems several problems are to be solved.

The first is that it is necessary to administer a sufficient dose to the patient taking into account the dilution and the dispersion in the organism, so that the significantly active portion that reaches the affected zone is effective.

The second is the latency period due to the metabolization and the diffusion in the organism before the molecule acts and the patient feels the benefits.

The third results from the sequelae that such a massive diffusion of the active molecule can cause in the organism, sequelae that are reflected by known secondary effects.

Thus, two known molecules, ibuprofen and ketoprofen, very effective anti-inflammatory agents, can be used to treat severe ailments of the buccopharyngeal cavity but with the sequelae expressed above.

Thus, for ibuprofen, it is possible to administer doses of 200 mg or more, and for ketoprofen, it is possible to administer doses of 50 mg of more so as to take into account the dilution in the organism.

It is also known that the beginning of the therapeutic effectiveness for the patient takes place at the earliest 45 minutes after intake, corresponding to the period of digestive absorption, metabolism and tissue diffusion.

The maximum concentration of the active ingredient in the blood is reached for ibuprofen after 90 minutes and for the ketoprofen at the end of 75 minutes, knowing that their respective pharmacological effects are of an approximately 2-hour duration for ibuprofen and a 1.5-hour duration for the ketoprofen.

As for secondary effects, they are produced by the diffusion of molecules in the vascular and tissue compartments of the organism since these molecules have a lipophilic nature imparting to them a high bioavailability.

These effects are reflected by nausea, vomiting, stomachaches, dyspepsias, hemorrhages that may or may not be occult, transit disorders of cutaneous or respiratory hypersensitivity reactions, dizziness or headaches, or else hepatic, renal or hematological secondary effects.

It is therefore noted that the secondary sequelae that are produced or are likely to be so by the absorption of such molecules are orders of magnitude different from the buccopharyngeal pains and inflammations, which can cause local invalidity.

The composition according to this invention, given by way of example, has as its object to overcome these problems by acting locally at the same level of the lesions and inflammations with very reduced dosages, therefore not being able to cause secondary effects and inducing an immediate therapeutic effect.

The composition according to the invention that is based on derivatives of the aryl-carboxylic family is now described in detail by highlighting the induced advantages and the solutions provided to problems posed by the currently proposed therapies.

To start with, it should be noted that there are several strong prejudices to be overcome in order to think about administering locally the derivatives of the aryl-carboxylic family. Actually, these active compounds are usually not very soluble in water and the biological media.

For the implementation of this type of composition, this induces a process that makes possible two effects, a priori antagonistic, the dissolution of the active ingredient despite its insoluble nature and its active diffusion that is facilitated through the mucous tissues thanks to its lipophilic nature.

In addition, the taste of the compounds that are retained as an example of implementation of the process is totally unacceptable, more particularly ibuprofen, and prohibits direct contact with the organs and the gustatory mucous membranes.

It is therefore advisable to resort to galenical formulations that ensure a slow diffusion, allowing the local buccopharyngeal usage, and, thanks to their complete dissolution, which ensure easy permucosal passage of the active ingredient so that it can ensure action at the level of the lesions in question.

The process consists in resorting to a salt of these compounds. In this case, the composition resorts to ibuprofen and to ketoprofen in the form of lysinate resulting from the combination of an amino acid, lysine, and ibuprofen and ketoprofen molecules.

These compounds are of the anti-inflammatory and peripheral analgesic type. They act on the mediators of the inflammation, namely the tissue enzymes, in particular the cyclo-oxygenases 1 and 2 and the prostaglandins.

Whereas the active ingredients ibuprofen and ketoprofen have a lipophilic nature, virtually insoluble in water, the forms of lysinates are completely water-soluble.

Thus, in the case of the composition according to this invention, the solubilization in the oral saliva occurs in a first step, and whereby the bond to the lysine salt is weak, the quick dissociation takes places in a second step and again imparts to the active ingredients their lipophilic nature.

This lipophilic nature then makes it possible for them to easily and passively pass through the cellular mucous membranes, they also being lipidic since they consist of phospholipids.

Having penetrated, these substances induce a blockage of tissue mediators of inflammation.

Then, so as to keep the active ingredient or ingredients in close contact with the mucous membranes in question, those of the buccopharyngeal cavity, it is advisable to formulate these active ingredients with at least one combined agent.

This first agent has as its role, in addition to creating a bioadhesive film on the mucous membranes, to slow down the dissolution and the release of the active ingredient in the saliva and to keep it in place locally so as to limit its loss by the act of swallowing.

Thus, this first agent is of the polymer type and simultaneously ensures with its actions a dissolution in the very midst of the polymer matrix.

This agent is selected from the following families:
1. Cellulose derivatives:
carboxy-methyl cellulose that contains soda,
hydroxy-ethyl cellulose
hydroxy-propyl cellulose,
hydroxy-propyl methyl cellulose or promellose, or
carboxy-methyl cellulose.
2. Gums:
guar,
xanthane, or
gum Arabic.
3. Polymers:
alginic acid and derivatives,
carboxy-vinyl polymer,
carbomer,
macrogols,
polyethylene glycol,
gelatin,
povidone, or
pectins.

This polymer agent is integrated into the final galenical form in proportions on the order of 2 to 20%.

The preferred galenical form that is retained for the administration of this composition is advantageously a slow-dissolving tablet taken by mouth.

For this purpose, a preferred substrate for the production of such a tablet is a soluble and very hydrophilic substrate. By these properties, its sole presence causes an osmotic flow in the mouth that facilitates the expression of the dissolved active ingredient.

This substrate represents the large majority of the finished tablet.

It is important during the production to provide a very strong homogeneity of the distribution of active ingredients.

Actually, it is necessary to avoid a significant localized supply due to a concentration that results from an irregularity of distribution because it is advisable that the active ingredient has been dissolved in the polymer fraction using water that it absorbs through its strongly hydrophilic properties and not in the oral cavity.

Since the polymers of the retained families are very avid for water, the active ingredients are not brought into direct contact with mucous membranes and there is no resurgence of the sense of taste before the permucosal passage.

In addition, too quick or too large a concentration of released active ingredient would create a saturation effect of the absorption capacity of the mucous membrane and would simultaneously induce recrystallizations of active ingredients and local ulcerations, which is not necessary and is even irritating, and therefore detrimental to good administration.

The combination of the substrate with the polymer agent makes it possible to avoid these saturation phenomena and to oppose the recrystallization of active ingredients by ensuring slow dissolution and uniform impregnation of the active ingredients by the mucous membrane. This combination also prevents the act of swallowing and the escape of the active ingredients via the digestive tract.

Thus, the conjugate effect of the substrate and the associated polymer agent exerts a double vector action of active ingredients and the mucous membrane protector against the risks of ulcerations of tissues brought into contact with the same active ingredients.

Such a substrate will be selected from among the family of carbohydrates:
lactose,
glucose,
saccharose,
sorbitol,
mannitol, and
xylitol.

Such a galenical formulation offers the advantage of imparting to the composition a pharmaceutical stability over time for the active ingredients that are used.

It is possible to cite two formulation examples with both of the two preferred active ingredients that are retained.

For a 1000 mg tablet:

| | |
|---|---|
| ibuprofen lysinate: | 25 mg |
| magnesium stearate: | 10 mg |
| talc: | 50 mg |
| aspartame: | 15 mg |
| metolose: | 70 mg |
| Arome: | 20 mg |
| sorbitol: | 810 mg |

For a 1000 mg tablet:

| | |
|---|---|
| ketoprofen lysinate: | 5 mg |
| magnesium stearate: | 10 mg |
| talc: | 50 mg |
| aspartame: | 15 mg |
| metolose: | 70 mg |
| Arome: | 20 mg |
| sorbitol: | 830 mg |

A tablet with such a composition can be produced industrially, without taking extreme precautions, in the following way:

Pour the components in the dry state into a rotating mixer after any clumps are broken up on a mesh with a mesh size of 1 to 2 mm, Mix these components for 10 to 20 minutes to ensure a very good homogeneity of distribution, Compress the mixture that is obtained in a tablet press to obtain a tablet that, when the patient takes it, dissolves within 1 to 5 minutes, and Packaging in blisters or in airtight tubes, known in the art.

Such a tablet makes it possible to administer a small dose of active ingredient, to obtain a uniform, slow and complete dissolution by arranging for it to stay in the mouth for an immediate effect and directly in contact with inflammatory lesions.

The process that was just described is not limited to the application that has just been given via two examples, but it is applied more generally for lipophilic molecules that can be administered by sublingual permucosal pathway, primarily at doses of less than 100 mg.

This makes it possible to preserve the benefit of attaining various vascular and tissue areas before undergoing the first hepatic degradation/metabolism.

It is possible to cite as molecules with local usage:
Anti-inflammatory molecules: bufexamac, diclofenac, flurbiprofen, flufenamic acid, indomethacin, mefenamic acid, naproxen, niflumic acid, sulindac, tenoxicam, or
Anti-mycotic molecules: econazole, fenticonazole, miconazole.

It is possible to cite as molecules that can benefit from the process to be administered via the sublinqual pathway:
Morphine analgesic molecules with central action: fentanyl
Anti-nausea, anti-allergic molecules: diphenhydramine.

Such compounds are sparingly soluble in water and the fact of administering them by perlingual pathway in the form of salts, in particular lysinate, makes possible a quick action, effective by eliminating the degradation linked to the digestive phase and by greatly reducing the administered doses.

In addition, it is possible to combine them for the simultaneous treatment of several ailments or for additional actions for the same ailment.

The invention claimed is:

1. A method for locally treating buccopharyngeal ailments in a subject in need thereof, comprising:
providing a composition comprising a non-steroidal anti-inflammatory drug (NSAID) in a water-soluble lysine-salt form, said composition being in tablet form, and comprising 2.5 wt % or less of the NSAID;
orally and locally administering the composition to the subject; and
allowing the composition to solubilize in the buccopharyngeal cavity of the subject, the composition being solubilized by the saliva of the subject, the lysine dissociating from the NSAID thereby imparting a lipophilic property to the NSAID, and said lipophilic NSAID actively diffusing through mucous tissues in the buccopharyngeal cavity of the subject without recrystallizing.

2. The method of claim 1, wherein when the composition is solubilized by the saliva, a bioadhesive film is created on the mucous membranes slowing down the dissolution and the release of the NSAID in the saliva and keeping the composition in place locally so as to limit loss of the composition by the act of swallowing.

3. The method of claim 1, wherein the NSAID is ibuprofen, or ketoprofen.

4. The method of claim 1, wherein the NSAID is ibuprofen.

5. The method of claim 1, wherein the NSAID in a water-soluble lysine-salt form is ibuprofen lysinate or ketoprofen lysinate.

6. The method of claim 1, wherein the composition comprises a substrate that makes possible a slow permucosal diffusion that is uniform and localized to the buccopharyngeal cavity.

7. The method of claim 6, wherein the substrate comprises a carbohydrate.

8. The method of claim 1, wherein the composition comprises a polymer agent that is selected from the group consisting of a cellulose derivative, a gum, alginic acid and derivatives, carboxy-vinyl polymer, carbomer, macrogol, polyethylene glycol, gelatin, povidone, and pectin.

9. The method of claim 1, wherein the composition has the following formulation:

| | |
|---|---|
| ibuprofen lysinate | 25 mg |
| magnesium stearate | 10 mg |
| talc | 50 mg |
| aspartame | 15 mg |
| hydroxy-propyl-methyl cellulose | 70 mg |
| Arome | 20 mg |
| sorbitol | 810 mg. |

10. The method of claim 1, wherein the composition has the following formulation:

| | |
|---|---|
| ketoprofen lysinate | 5 mg |
| magnesium stearate | 10 mg |
| talc | 50 mg |
| aspartame | 15 mg |
| hydroxy-propyl-methyl cellulose | 70 mg |
| Arome | 20 mg |
| sorbitol | 830 mg. |

11. The method of claim 1, wherein the composition comprises 25 mg or less of the NSAID in a water-soluble lysine-salt form.

12. The method of claim 1, wherein the composition is administered to the buccopharyngeal cavity of the subject.

13. The method of claim 1, wherein the buccopharyngeal ailment is a lesion or inflammation.

* * * * *